US009037477B2

(12) United States Patent
Bardy et al.

(10) Patent No.: US 9,037,477 B2
(45) Date of Patent: May 19, 2015

(54) COMPUTER-IMPLEMENTED SYSTEM AND METHOD FOR EVALUATING AMBULATORY ELECTROCARDIOGRAPHIC MONITORING OF CARDIAC RHYTHM DISORDERS

(75) Inventors: Gust H. Bardy, Carnation, WA (US); Jon Mikalson Bishay, Seattle, WA (US)

(73) Assignee: CARDIAC SCIENCE CORPORATION, Waukesha, WI (US)

( * ) Notice: Subject to any disclaimer, the term of this patent is extended or adjusted under 35 U.S.C. 154(b) by 82 days.

(21) Appl. No.: 12/901,461

(22) Filed: Oct. 8, 2010

(65) Prior Publication Data

US 2012/0088998 A1  Apr. 12, 2012

(51) Int. Cl.
*G06Q 50/00* (2012.01)
*A61B 5/00* (2006.01)
*A61B 5/0402* (2006.01)
(Continued)

(52) U.S. Cl.
CPC .............. *A61B 5/0006* (2013.01); *A61B 5/0402* (2013.01); *A61B 5/0432* (2013.01); *A61B 2562/08* (2013.01); *G06F 19/322* (2013.01); *G06F 19/327* (2013.01); *G06F 19/3425* (2013.01)

(58) Field of Classification Search
CPC ........................................... G06Q 50/22–50/24
USPC ......................................................... 705/2–3
See application file for complete search history.

(56) References Cited

U.S. PATENT DOCUMENTS 3,215,136 A   11/1965 Holter et al.
4,123,785 A   10/1978 Cherry et al.
(Continued)

FOREIGN PATENT DOCUMENTS

DE        19955211        5/2001
WO        03032192        4/2003
(Continued)

OTHER PUBLICATIONS

Lieberman Jonathon, "How Telemedicine Is Aiding Prompt ECG Diagnosis In Primary Care," British Journal Of Community Nursing, vol. 13, No. 3, Mar. 1, 2008, pp. 123-126, XP009155082, ISSN: 1462-4753.
(Continued)

*Primary Examiner* — Jonathan K Ng
(74) *Attorney, Agent, or Firm* — Patterson Thuente Pedersen, P.A.

(57) ABSTRACT

A computer-implemented method for evaluating ambulatory electrocardiographic (ECG) monitoring of cardiac rhythm disorders is provided. A patient is registered online and medical records for the patient are assembled. An ambulatory ECG monitor that includes leadless integrated sensing electrodes independently suspended from a flexible housing, is registered to the patient. An electrocardiogram is retrieved from the recording circuitry. The electrocardiogram and the medical records are evaluated against diagnostic criteria. Upon making a finding when the diagnostic criteria is met, the patient is referred to a cardiac rhythm specialist online, which includes sending the cardiac rhythm abnormality finding. As a result, both physicians and patients enjoy an ease-of-use not found with conventional ambulatory ECG monitors. By bypassing determining whether a referral is needed and separately establishing the referral, patients can be treated more completely and more rapidly than through conventional patient referral, especially for serious illness, with less cost and less delay.

20 Claims, 8 Drawing Sheets

(51) Int. Cl.
    *A61B 5/0432* (2006.01)
    *G06F 19/00* (2011.01)

(56) References Cited

U.S. PATENT DOCUMENTS

| | | |
|---|---|---|
| 4,532,934 A | 8/1985 | Kelen |
| 4,550,502 A | 11/1985 | Grayzel |
| 4,716,903 A | 1/1988 | Hansen |
| 4,809,705 A | 3/1989 | Ascher |
| 4,915,656 A | 4/1990 | Alferness |
| 5,168,876 A | 12/1992 | Quedens et al. |
| 5,215,098 A | 6/1993 | Steinhaus |
| D341,423 S | 11/1993 | Bible |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,458,141 A | 10/1995 | Neil |
| 5,473,537 A | 12/1995 | Glazer et al. |
| 5,579,919 A | 12/1996 | Gilman et al. |
| 5,582,181 A | 12/1996 | Ruess |
| D377,983 S | 2/1997 | Sabri et al. |
| 5,623,935 A | 4/1997 | Faisandier |
| 5,697,955 A | 12/1997 | Stolte |
| 5,749,902 A | 5/1998 | Olson et al. |
| 5,817,151 A | 10/1998 | Olson et al. |
| 5,850,920 A | 12/1998 | Gilman et al. |
| D407,159 S | 3/1999 | Roberg |
| 5,906,583 A | 5/1999 | Rogel |
| 5,951,598 A | 9/1999 | Bishay et al. |
| 5,984,102 A | 11/1999 | Tay |
| 6,101,413 A | 8/2000 | Olson et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,269,267 B1 | 7/2001 | Bardy et al. |
| 6,272,385 B1 | 8/2001 | Bishay et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,418,342 B1 | 7/2002 | Owen et al. |
| 6,427,083 B1 | 7/2002 | Owen et al. |
| 6,456,872 B1 | 9/2002 | Faisandier |
| 6,546,285 B1 | 4/2003 | Owen et al. |
| 6,605,046 B1 | 8/2003 | Del Mar |
| 6,607,485 B2 | 8/2003 | Bardy |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,754,523 B2 | 6/2004 | Toole |
| 6,782,293 B2 | 8/2004 | Dupelle et al. |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| D558,882 S | 1/2008 | Brady |
| 7,328,061 B2 | 2/2008 | Rowlandson et al. |
| 7,412,395 B2 | 8/2008 | Rowlandson et al. |
| D606,656 S | 12/2009 | Kobayashi et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,231,539 B2 | 7/2012 | Bardy |
| 8,231,540 B2 | 7/2012 | Bardy |
| 8,239,012 B2 | 8/2012 | Felix et al. |
| 8,260,414 B2 | 9/2012 | Nassif et al. |
| 8,266,008 B1 * | 9/2012 | Siegel et al. ............... 705/26.1 |
| 8,277,378 B2 | 10/2012 | Bardy |
| 8,285,370 B2 | 10/2012 | Felix et al. |
| 8,308,650 B2 | 11/2012 | Bardy |
| 8,366,629 B2 | 2/2013 | Bardy |
| 2002/0120310 A1 * | 8/2002 | Linden et al. ............... 607/60 |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0139785 A1 * | 7/2003 | Riff et al. ............... 607/60 |
| 2004/0008123 A1 * | 1/2004 | Carrender et al. ....... 340/825.49 |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0087836 A1 | 5/2004 | Green et al. |
| 2004/0148194 A1 | 7/2004 | Wellons et al. |
| 2004/0243435 A1 | 12/2004 | Williams |
| 2004/0256453 A1 | 12/2004 | Lammle |
| 2004/0260188 A1 | 12/2004 | Syed et al. |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0228243 A1 | 10/2005 | Bardy |
| 2005/0245839 A1 | 11/2005 | Stivoric et al. |
| 2006/0025824 A1 | 2/2006 | Freeman et al. |
| 2006/0041201 A1 | 2/2006 | Behbehani et al. |
| 2006/0100902 A1 * | 5/2006 | Glimp et al. ............... 705/2 |
| 2006/0122469 A1 | 6/2006 | Martel |
| 2006/0224072 A1 | 10/2006 | Shennib |
| 2006/0235320 A1 | 10/2006 | Tan et al. |
| 2006/0253006 A1 | 11/2006 | Bardy |
| 2007/0003115 A1 * | 1/2007 | Patton et al. ............... 382/128 |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100667 A1 | 5/2007 | Bardy |
| 2007/0123801 A1 | 5/2007 | Goldberger et al. |
| 2007/0136091 A1 * | 6/2007 | McTaggart ............... 705/2 |
| 2007/0179357 A1 | 8/2007 | Bardy |
| 2007/0203415 A1 | 8/2007 | Bardy |
| 2007/0203423 A1 | 8/2007 | Bardy |
| 2007/0225611 A1 | 9/2007 | Kumar et al. |
| 2007/0244405 A1 * | 10/2007 | Xue et al. ............... 600/523 |
| 2007/0249946 A1 | 10/2007 | Kumar et al. |
| 2007/0255153 A1 * | 11/2007 | Kumar et al. ............... 600/515 |
| 2007/0265510 A1 | 11/2007 | Bardy |
| 2007/0276270 A1 | 11/2007 | Tran |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2008/0051668 A1 | 2/2008 | Bardy |
| 2008/0058661 A1 | 3/2008 | Bardy |
| 2008/0139953 A1 | 6/2008 | Baker et al. |
| 2008/0194927 A1 | 8/2008 | KenKnight et al. |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |

(56) References Cited

U.S. PATENT DOCUMENTS

| | | |
|---|---|---|
| 2009/0069867 A1 | 3/2009 | KenKnight et al. |
| 2009/0216132 A1 | 8/2009 | Orbach |
| 2009/0270747 A1* | 10/2009 | van Dam et al. ............ 600/509 |
| 2009/0292194 A1 | 11/2009 | Libbus et al. |
| 2010/0022897 A1 | 1/2010 | Parker et al. |
| 2010/0070296 A1* | 3/2010 | Massoumi et al. ............ 705/2 |
| 2010/0081913 A1 | 4/2010 | Cross et al. |
| 2010/0185063 A1 | 7/2010 | Bardy |
| 2010/0191154 A1 | 7/2010 | Berger et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0101396 A1* | 4/2012 | Solosko et al. ............ 600/509 |
| 2012/0108917 A1* | 5/2012 | Libbus et al. ............ 600/301 |
| 2012/0302906 A1 | 11/2012 | Felix et al. |
| 2013/0123651 A1 | 5/2013 | Bardy |
| 2013/0158361 A1 | 6/2013 | Bardy |

FOREIGN PATENT DOCUMENTS

| | | |
|---|---|---|
| WO | 2006014806 | 2/2006 |
| WO | 2007092543 | 8/2007 |
| WO | WO2008/010216 A1 | 1/2008 |
| WO | WO2009/112976 A1 | 9/2009 |
| WO | WO2009/112978 A1 | 9/2009 |
| WO | WO2009/112979 A1 | 9/2009 |
| WO | 2010066507 | 6/2010 |

OTHER PUBLICATIONS

P. Libby et al., "Braunwald's Heart Disease—A Textbook of Cardiovascular Medicine," Chs. 11, pp. 125-148 and 12, pp. 149-193 (8th ed. 2008), American Heart Association.

Sittig et al., "A Computer-Based Outpatient Clinical Referral System," International Journal Of Medical Informatics, Shannon, IR, vol. 55, No. 2, Aug. 1, 1999, pp. 149-158, XO004262434, ISSN: 1386-5056(99)00027-1.

Epstein, Andrew E. et al.; ACC/AHA/HRS 2008 Guidelines for Device-Based Therapy of Cardiac Rhythm Abnormalities. J. Am. Coll. Cardiol. 2008; 51; e1-e62, 66 pages.

Kligfield, Paul et al., Recommendations for the Standardization and Interpretation of the Electrocardiogram: Part 1. J.Am. Coll. Cardiol; 2007; 49; 1109-27, 75 pages.

EPO Extended Search Report for Application No. 11184382.7-2201, Dated Jan. 23, 2012, 11 Pgs.

EPO Extended Search Report for Application No. 11184379.3-1225, Dated Jan. 26, 2012, 6 Pgs.

EPO Extended Search Report for Application No. 11184344.7-1265/2438852, Dated Jun. 6, 2012, 6 Pgs.

EPO Extended Search Report for Application No. 11184341.3-1265/2438851, Dated Jun. 8, 2012, 6 Pgs.

EPO Extended Search Report for Application No. 11184353.8-1265/2438854, Dated Nov. 7, 2012, 10 Pgs.

EPO Extended Search Report for Application No. 11184347.0-1265/2438853, Dated Nov. 7, 2012, 11 Pgs.

EPO Extended Search Report for Application No. 11184156.5-2319/2438848 Dated Apr. 27, 2012, 10 Pgs.

Chen et al., "Monitoring Body Temperature Of Newborn Infants At Neonatal Intensive Care Units Using Wearable Sensors," BodyNets'2010, Corfu Island, Greece. (Sep. 10-12, 2010).

Lauren Gravita, "When Your Diet Needs A Band-Aid," Technology Review, MIT. (May 1, 2009).

15 Of The Hottest Wearable Gadgets—http://thehottestgadgets.com/2008/09/the-15-hottestest-wearable-gadgets-001253.

US 6,527,714, 03/2003, Bardy (withdrawn)

* cited by examiner

Fig. 2 (Con'd).
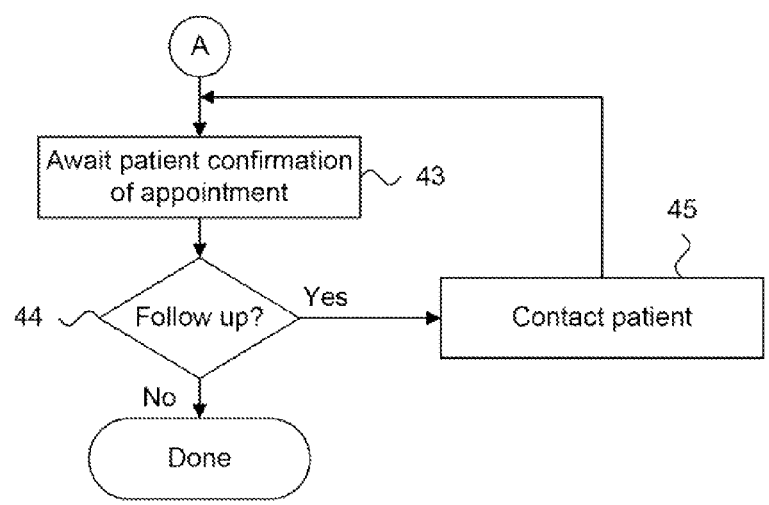

COMPUTER-IMPLEMENTED SYSTEM AND METHOD FOR EVALUATING AMBULATORY ELECTROCARDIOGRAPHIC MONITORING OF CARDIAC RHYTHM DISORDERS

FIELD

This application relates in general to ambulatory electrocardiographic monitoring and, in particular, to a computer-implemented system and method for evaluating ambulatory electrocardiographic monitoring of cardiac rhythm disorders.

BACKGROUND

Cardiologists are experts in the diagnosis and treatment of heart rhythm disorders, such as tachycardia (excessively fast and abnormal heart rates) and bradycardia (excessively slow and abnormal heart rates). Disorders of the heart's electrical system are the primary cause of heart rhythm disorders, which, in turn, cause ineffective pumping of the blood, thereby placing a patient at risk of loss of consciousness and sudden death. Under managed care, access to medical specialists, such as cardiologists and cardiac electrophysiologists (cardiologists who focus purely on the heart's electrical system), requires a patient's primary care provider to first make a referral. Primary care physicians typically undertake their own diagnostic testing and screening before referring a patient. Evaluating the patient thoroughly often involves the ordering of tests. Each step preceding cardiac specialist referral, though, adds on an additional 30 percent of administrative overhead costs on average, while a failure by a primary care provider to act may force patients to seek assistance through the emergency room, thereby increasing emergency services' already overwhelming burden.

The diagnosis of cardiac rhythm disorders is challenging to address in the brief period of in-clinic exposure to the primary care provider due to the intermittent and variable nature of most heart rhythm disorders. Moreover, a patient's symptoms, such as syncope, presyncope, palpitations, angina, dyspnea, and fatigue, are consistent with many health problems, other than heart rhythm disorders, including benign causes. The ability of a primary care provider to make the appropriate diagnosis can be extremely challenging and the tools to aid in this diagnosis difficult to access. Moreover, an overall decline in the skills required to diagnose and treat heart rhythm disease in the general medical community has made primary care providers ill-equipped to make the kinds of classic arrhythmia diagnoses required to prevent or treat a serious illness. Furthermore, primary care providers are artificially limited in their ability to make patient referrals to cardiac specialists due to managed care restrictions, third-party provider rules, and practical obstacles in accessing needed diagnostic tools that are usually not in the same physical location as the primary care provider.

Current forms of diagnostic testing available in-clinic to primary care providers, typically only the standard 12-lead electrocardiogram (ECG), are inadequate to identify cardiac rhythm disorders in the context of today's limitations in time, finances, and obstacles in the patient referral network. For instance, the conventional 12-lead ECG test is merely a "snapshot" of a patient's heart rhythm, lasting approximately 10 seconds. While 12-lead ECG testing can identify many forms of persistently-presented heart disease, 12-lead ECG testing is of nominal assistance in identifying episodic heart rhythm disorders that rarely are present during clinic visits.

Other forms of ECG testing are more effective at identifying cardiac rhythm disorders but are seldom ordered by primary care providers because of the administrative and cost hurdles incurred in attempting the use of such tools. For instance, U.S. Pat. No. 3,215,136 issued Nov. 2, 1965 to Holter et al. discloses an electrocardiographic recording and playback means, more commonly known as a "Holier monitor" named after its inventor, Norman Holter in 1949. Holter monitor is now used synonymously with long-term heart rhythm recording, usually lasting at least 24 hours. With use of a Holter monitor, episodes of ventricular tachycardia, asystolic intervals, and ectopic heart beats are sensed and recorded by electrodes placed on the patient's skin. ECG rhythm disturbances recorded by the Holter monitor can then be identified. In less constrained times, such abnormalities would be seen by cardiologists, who have been contracted to overread the Holter recordings and provide diagnostic information to the referring primary care provider. These cardiologists would, in turn, care for the patient should a serious rhythm disorder be identified. Times have changed, however, and this older model of health care is no longer easily used or, if used, taken to the next step of referral and care by a cardiac specialist because of logistical and cost constraints.

The value of ambulatory ECG or Holter monitoring and the appropriate use of this technology, especially by primary care providers, suffers from several drawbacks. First, under managed care, ambulatory ECG monitoring is usually physically inaccessible to primary care providers in their offices. Such monitoring requires a referral to a testing laboratory, plus an additional referral to a cardiologist to interpret any findings, presuming the results of the Holter recording actually make their way back to the referring primary care provider, which is not necessarily a guaranteed event. Further obstacles arise by virtue of the need for the patient to be compliant with accessing, properly using, and returning the monitor to the pickup location, as well as communication burdens that arise between the referring physician, the overseeing cardiologist, and feedback to the patient following the outcome of the test. This communication complexity often leads to patients either not receiving the diagnostic equipment, not having the test results communicated to them, or not having an appropriate follow up with a knowledgeable physician. Too commonly, no one calls the patient post-monitoring. In essence, the patient is left outside the health care channel and must wait until, and if, he is informed of test results and follow up care. In addition, the reading of recorded ECG data usually requires an analysis by a heart disease specialist, which incurs additional cost and loss of time in making the patient diagnosis. Such back-end burdens can dissuade or even prevent a primary healthcare physician from ordering ambulatory ECG monitoring in the first place.

U.S. Patent application, Publication No. 2007/0255153, filed Nov. 1, 2007, to Kumar et al.; U.S. Patent application, Publication No. 2007/0225611, filed Feb. 6, 2007, to Kumar et al.; and U.S. Patent application, Publication No. 2007/0249946, filed Feb. 6, 2007, to Kumar et al. disclose a non-invasive cardiac monitor and methods of using continuously recorded cardiac data. A heart monitor suitable for use in primary care includes a self-contained and sealed housing. Continuously recorded cardiac monitoring is provided through a sequence of simple detect-store-offload operations that are performed by a state machine. The housing is adapted to remain affixed to a mammal from at least seven days up through four weeks. The heart monitor can include an activation or event notation button, the actuation of which increases the fidelity of the ECG information stored in the memory. The monitor is specifically intended to provide monitoring continuously and without interruption over an extended period, after which the stored information can be retrieved and analyzed offline to identify ECG events, including determining the presence of an arrhythmia.

Finally, U.S. Patent application, Publication No. 2008/0284599, filed Apr. 28, 2006, to Zdeblick et al. and U.S. Patent application, Publication No. 2008/0306359, filed Dec. 11, 2008, to Zdeblick et al., disclose a pharma-informatics system for detecting the actual physical delivery of a pharmaceutical agent into a body. An integrated circuit is surrounded by pharmacologically active or inert materials to form a pill, which dissolve in the stomach through a combination of mechanical action and stomach fluids. As the pill dissolves, areas of the integrated circuit become exposed and power is supplied to the circuit, which begins to operate and transmit a signal that may indicate the type, A signal detection receiver can be positioned as an external device worn outside the body with one or more electrodes attached to the skin at different locations. The receiver can include the capability to provide both pharmaceutical ingestion reporting and psychological sensing in a form that can be transmitted to a remote location, such as a clinician or central monitoring agency.

Therefore, a need remains for a way to provide primary care providers with direct on-hand access to ambulatory ECG monitoring without adding significant procedural obstacles, cost or time burdens, and which work within the confines of managed care, while simultaneously providing important diagnostic information and appropriate care directly to the patient through a closed health care loop.

SUMMARY

A computer-implemented system and method for inexpensive and readily accessible ambulatory ECG monitoring is provided. The ambulatory ECG monitoring is particularly adapted for use in managed healthcare by primary care physicians and their patients. Each ambulatory ECG monitor includes leadless sensing electrodes and low cost recording circuitry for short term or extended wear monitoring. The patient wears the monitor for a set observation period and preferably maintains an electronic, vocal, or paper diary contemporaneous to monitoring. A unique identifier is assigned to the monitor that is used throughout the remainder of the diagnosis and referral process. The patient sends the monitor (or its ECG data recordings) and diary, if created, to a monitoring, consultation, and specialist referral center ("referral center") that retrieves and evaluates the recorded ECG data. In one embodiment, the referral center retains a cardiac specialist to interpret any ectopic findings and provide a formal medical diagnosis. As a key and unique feature of this system, when appropriate, the patient is directly referred by the referral center to a cardiac specialist and an appointment is set up for definitive patient evaluation and care, if the monitoring results indicate, rather than having the patient report back to his primary care physician. Additionally, the patient can proactively track the status of and make inquiries concerning his test results through the unique identifier, rather than relying on his primary care provider's office staff or the physician himself. The primary care physician is also informed, but is not required to be involved in any manner. This process results in a rapid diagnosis, and importantly, rapid access to a specialist, who can initiate definitive patient care, when needed while enabling the patient to play an active role throughout each stage of the monitoring process.

One embodiment provides a computer-implemented method for evaluating ambulatory electrocardiographic (ECG) monitoring of cardiac rhythm disorders. A patient is registered online and medical records for the patient are assembled. An ambulatory ECG monitor that includes leadless integrated sensing electrodes independently suspended from a flexible housing that encloses ECG recording circuitry connected to the electrodes, is registered to the patient. An electrocardiogram is retrieved from the recording circuitry. The electrocardiogram and the medical records for the patient are evaluated against diagnostic criteria, which includes statistical correlations of cardiac disease states and cardiac rhythm patterns. Upon making a finding of a cardiac rhythm abnormality when the diagnostic criteria is met, the patient is referred to a cardiac rhythm specialist online, which includes sending the cardiac rhythm abnormality finding.

A further embodiment provides a computer-implemented method for diagnosing cardiac rhythm disorders through recorded ambulatory electrocardiograms. A patient is registered online with a referral center. Medical records for the patient are assembled in a centralized database maintained by the referral center. A tracking number is assigned to the monitor in relation to the ambulatory electrocardiographic (ECG) monitoring and the tracking number is matched to the patient in the database. An ambulatory ECG monitor that includes leadless integrated sensing electrodes independently suspended from a flexible housing that encloses ECG recording circuitry connected to the electrodes, is registered to the patient. Following completion of ambulatory ECG monitoring by the patient, analysis and referral are performed through the referral center. A status is provided upon demand regarding the analysis and referral to the patient keyed to the tracking number. An electrocardiogram is retrieved from the recording circuitry. The electrocardiogram and the medical records for the patient are evaluated against diagnostic criteria, which includes statistical correlations of cardiac disease states and cardiac rhythm patterns. Upon making a finding of a cardiac rhythm abnormality when the diagnostic criteria is met, direct referral is undertaken. An appointment for the patient is set with a cardiac rhythm specialist online, which includes sending the electrocardiogram, medical records, and cardiac rhythm abnormality finding. The patient is notified of the appointment with confirmation.

A still further embodiment provides a computer-implemented method for automated diagnosis and follow up ambulatory electrocardiographic monitoring. A patient is enrolled in a referral center. An ambulatory electrocardiographic monitor is registered to the patient. An electrocardiogram is retrieved from the recording circuitry of the ambulatory electrocardiographic monitor following ambulatory monitoring. The electrocardiogram is evaluated against diagnostic criteria, which include statistical correlations of cardiac disease states and cardiac rhythm patterns appearing in the electrocardiogram during the ambulatory monitoring. Follow up care of the patient is performed through the referral center based on outcomes from the evaluation of the electrocardiogram.

Primary care physicians are empowered with a type of ambulatory ECG monitoring that, in conjunction with a referral center, ensures proper data interpretation and medical follow up. A primary care physician need only apply an ambulatory ECG monitor in-clinic or provide a monitor to a patient through a prescription called into a pharmacy or other dispensary point-of-sale. Subspecialty expertise in arrhythmia diagnosis need not be resident in the provider's clinic, nor must the patient be referred to a separate ambulatory ECG testing laboratory. The low cost of each monitor encourages use when patient symptoms urge access to ambulatory ECG monitoring data. The backup system of support for the general physician helps minimize the risk of misdiagnosis and the need to even establish a referral, which is often not a simple decision or a simple process to ensure. Additionally, the combination of low cost and convenience of access to expertise encourages testing when appropriate to evaluating new medications or other changes important for the conduct of high-quality medical care.

Another key feature is that patients are empowered with the ability to self-screen a potential arrhythmic condition through ambulatory ECG monitoring. Access to cardiac rhythm expertise is difficult for a variety of reasons. Patients save both the costs and inconvenience of undertaking intermediate diagnostic testing, as typically required when undergoing conventional Holter-type ambulatory ECG monitoring, as well as avoid the risk of non-reimbursement that arises when they seek help outside their managed care plan. Patients are able to stay informed of their test results and follow on care without having to passively wait for follow up to occur. Moreover, wasted time is avoided by all interested parties.

Finally, as part of the system employed by primary care providers, cardiac specialists are empowered with receiving complete patient referrals and critical ECG data that enable them to effectively diagnose and treat arrhythmic conditions without the usual repetitive phone calls and requests to access medical information between doctors offices. Medical information and patient-generated diary entries are communicated to the referral center as part of the ambulatory ECG monitoring process, which is provided to cardiac specialists as part of a complete referral.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

To the average internal medicine or family practice physician, conventional forms of ambulatory ECG monitoring are only indirectly accessible and are rarely used because of the cost and inconvenience of access, diagnosis and follow-up referral to patient and physician alike. This situation hampers the evaluation of patients with sporadic symptoms like syncope, palpitations, and, dyspnea, that are often not present at the time of visiting the doctor. Equipping these physicians with proper diagnostic tools is critical to proper patient management. Such tools must he highly-accessible, yet low-cost to ensure use when needed. At the same time, patients need a sense of transparency in healthcare provisioning. Undertaking diagnostic testing is an accepted part of the healthcare process, yet once testing has been completed, patients can feel that they are at the mercy of the healthcare system in terms of receiving follow up information and guidance. Such feelings of helplessness are only exacerbated as the waiting time for information and referral after test completion continues for days or weeks.

Figure 1:
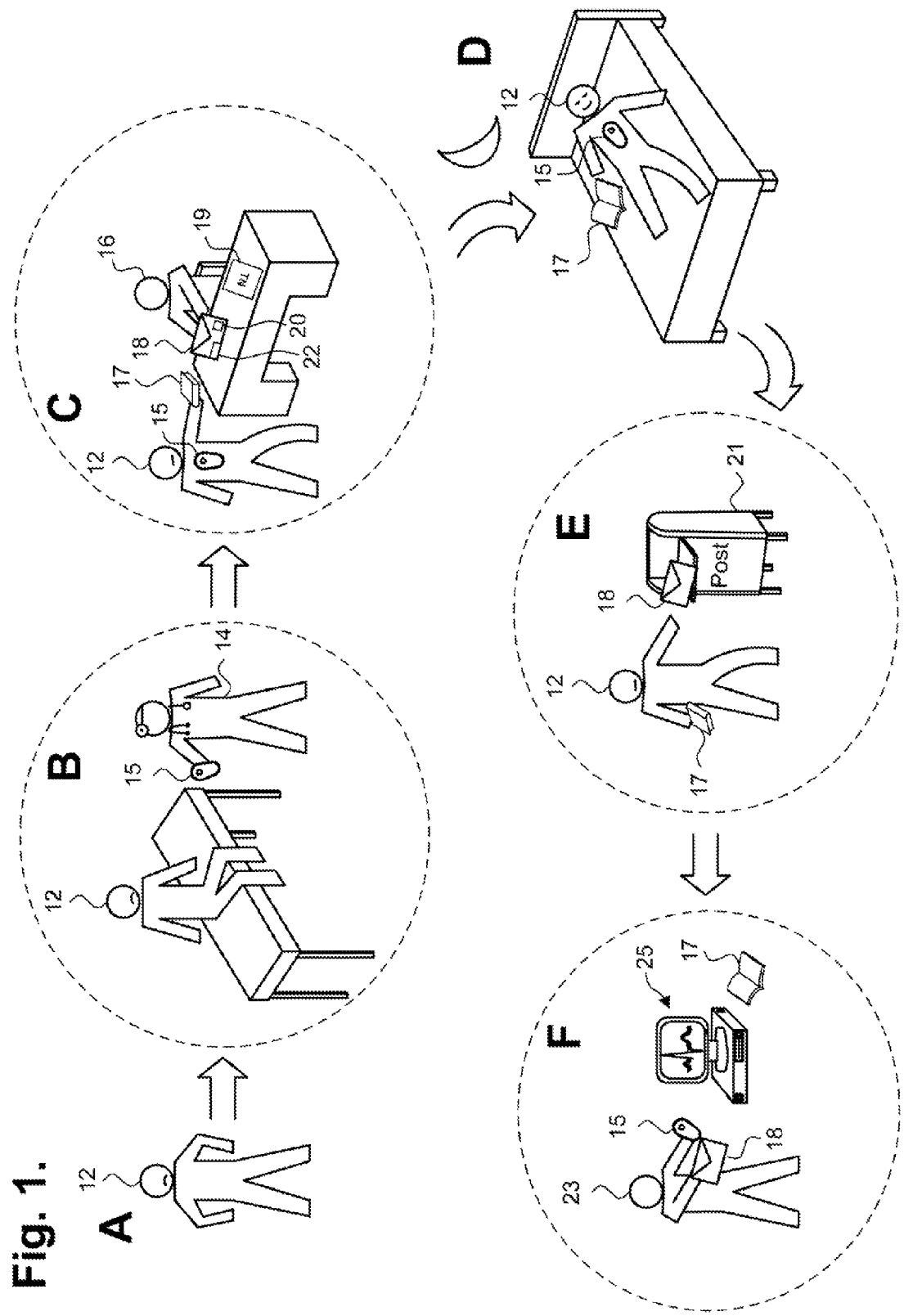
FIG. 1 is a diagram showing, by way of example, a method for evaluating ambulatory electrocardiographic monitoring of cardiac rhythm disorders in accordance with one embodiment.

Both of these primary care physician and patient needs can be met through a system that forms a closed-loop using ambulatory ECG monitoring. FIG. 1 is a diagram showing, by way of example, a method for evaluating ambulatory electrocardiographic monitoring of cardiac rhythm disorders 10 in accordance with one embodiment. Briefly, an ambulatory ECG monitor is packaged as an adhesive patch that can be applied in-clinic by a primary care provider, or at home by the patient. ECG data is recorded and subsequently read by a monitoring, consultation, and specialist referral center ("referral center") with which the patient can automatically be enrolled using tracking information specific to the patient and embedded into the monitor using, for instance, a radio frequency identification tag. Based on the recorded ECG data, diagnosis and referral to cardiac or other medical specialists, as appropriate, are made. The referrals are made by the referral center, not the physician who applied or prescribed the ECG monitor. Likewise, the referrals do not require further in-clinic primary care services, which is a key feature of that is particularly helpful to the patient. Moreover, the patient can track and make inquires regarding the status of his test results on demand throughout each stage of diagnosis and referral by tracking the information and the results of the information contained in his ECG monitor. Thus, by assuring access to expert medical specialist referral by automatically scheduling an appointment for the patient with the most pertinent physician based on the patient's ECG findings and by enabling the patient to be a part of the post-monitoring process, the key omissions in conventional patient management are resolved.

The scenario for use will take the following course. A patient 12, possibly suffering from cardiac arrhythmia, experiences classic symptoms, such as syncope, presyncope, palpitations, angina, dyspnea, and fatigue (step A) will become concerned and sees his primary care physician 14 for an in-clinic appointment. During the appointment, the physician 14 or an assistant, such as a nurse, applies an ambulatory ECG monitor 15 to the patient's chest when presented with indications for ambulatory ECG monitoring (step B), as further described below with reference to FIG. 4. (The size of the monitor 15 in FIG. 1 et seq. is exaggerated for clarity.) Alternatively, the physician 14 may give the patient 12 the monitor 15 to be applied later on by the patient 12 himself or by an assistant in another place, such as at home. In a further embodiment, the patient 12 could self-screen by obtaining an ambulatory ECG monitoring kit over-the-counter or, if required, under a prescription called into a pharmacy by his primary care physician, such as described in commonly-assigned U.S. Patent application, entitled "Computer-Implemented System and Method for Mediating Patient-Initiated Physiological Monitoring," Ser. No. 12/901,455, filed Oct. 8, 2010, pending, the disclosure of which is incorporated by reference. The self-screening monitoring kit would include instructions on how to either physically return the monitor 15 or to electronically transfer the recorded physiological data from the monitor 15 to the referral center following monitoring.

Either prior to seeing the physician 14 or following application of the monitor 15, the patient 12 is registered with the referral center, if he was not already registered before. The patient 12 also receives instructions, such as from his physician's nurse 16, regarding physically sending the monitor 15 (or its ECG data recordings) to the referral center following monitoring and on how to track the status of the test results and follow on care online (step C). A tracking number ("TN") 19 is assigned to the monitor 15 that follows the monitor 15 throughout monitoring of the heart beat, reading its output, follow up, diagnosis and referral, which is also provided to the patient 12. The nurse 16 electronically matches the tracking number 19 to the patient 12 in a database centrally maintained by the referral center online. The nurse 16 also uploads the patient's personal medical information, thereby creating a complete medical record that can be used by a cardiac specialist in the event of referral.

In one embodiment, the patient 12 is given a sealable envelope 18 or similar container in which to physically enclose and send off the used monitor 15 to the referral center. The envelope 18 includes an RFID tag 20 and a detachable tracking ticket 22. The nurse 16 uses an RFID transceiver-equipped computer, including a desktop, notebook, or tablet computer, or mobile computing device, such as a smart telephone, to read from and record into the RFID tag 22. The computer includes those components conventionally found in general purpose programmable devices, such as a central processing unit, volatile memory, input and output ports, user display, keyboard or other input device, network interface, and non-volatile mass storage. Other components are possible. The nurse 16 records the tracking number 19 into the envelope's RFID tag 20 and onto the tracking ticket 22. Alternatively, the tracking number 19 could originate as a pre-generated code already printed on the tracking ticket 22 and be recorded into both the envelope's RFID tag 20 and an RHO tag provided with the monitor 15, as further described infra. The patient 12 is instructed to detach the tracking ticket 22 on which the tracking number 19 has been recorded prior to sending off the monitor 15. In a further embodiment, the patient 12 electronically transmits the recorded ECG data to the referral center following completion of monitoring.

At the same time that post-monitoring instructions are received, the patient 12 is given a diary 17 to help chronicle physical symptoms, subjective feelings, and activities at the time of symptomatic onset during monitoring. A related challenge facing physicians is a lack of contemporaneous subjective data from the patient himself concerning his complaints at the time of occurrence. To address this concern, the patient 12 is expected to maintain the diary 17 throughout the time that the monitor 15 is worn. In one embodiment, the patient 12 is either provided with a form of electronic or traditional paper diary 17 or instructed on accessing a dictation service that makes diary entries for the patient. In a further embodiment, where the patient obtains a monitor 15 over-the-counter or through a prescription called in by the primary care provider 14, the monitoring kit includes a diary 17.

The diary 17 can be implemented in the form of software, technology-assisted dictation, or conventional writing that is later electronically transcribed. A software-implemented diary can be provided in several forms. For instance, the diary software could be distributed on machine-readable media, or downloaded online, which, when installed on a computing device, locally executes an electronic diary application. The computing device can be a computer workstation, personal computer, personal digital assistant, programmable or "smart" mobile telephone, such as an iPhone or Blackberry, respectively licensed by Apple Inc., Cupertino, Calif. and Research In Motion, Waterloo, Ontario, Canada, intelligent digital media player, mobile tablet computer, or other programmable stationary or portable electronic device. The computer includes those components conventionally found in general purpose programmable devices, such as a central processing unit, volatile memory, input and output ports, user display, keyboard or other input device, network interface, and non-volatile mass storage. Other components are possible. Alternatively, the diary software could be a virtual application loaded from a remote server, such as a Web-based application that executes in a Web browser on the patient's computing device. As well, the diary software could be part of an existing software application, like a personal information manager and communications program, such as Outlook, licensed by Microsoft Corporation, Redmond, Wash., or a social networking and microblogging service, such as Twitter, licensed by Twitter, Inc., San Bruno, Calif. Preferably once a day or as appropriate, the patient 12 types or dictates entries into the diary 17. A technology-assisted dictated diary uses an existing electronics infrastructure to accept spoken diary entries from the patient 12, who is asked to telephone a call monitoring center to dictate his diary entries daily. This form of diary is particularly apropos for those patients who lack access to or knowledge of using a computing device. When dictated, voice recognition software executing at the call center converts patient's spoken words into text, or the speech can be manually transcribed into text off-line by a third party transcription service. A conventional written diary is typically a bound notebook or other form of printed material into which the patient 12 manually chronicles his daily activities and physical complaints. Diary entries are later converted into electronic form by the referral center or a third party transcription service. Other forms of diary are also possible.

During monitoring (step D), the patient 12 engages in activities of daily living, while the monitor 15 unobtrusively monitors and records ECG data. Continuous and uninterrupted wear of the monitor 15 over the entire course of monitoring may be impracticable for every patient. Skin sensitivities, allergies, irritation, and similar factors have an effect on a patient's ability to tolerate the wearing of the monitor 15 for an extended period. Similarly, oil on the skin's surface, perspiration, and overall physical hygiene can affect monitor adhesion. Thus, each monitor 15 includes a flexible housing and standoff-separated skin adhesion assembly. The housing can be separated from the skin adhesion assembly to allow the patient 12 to reposition or replace the skin adhesion assembly. Either the same housing or a new housing can be used during successive periods of monitoring. When the same housing is reused, the recording circuitry compensates for disconnection and reconnection of the sensing electrodes by stopping recording of ECG data during the gap in monitoring, as sensed by disconnection from the set of sensing electrodes. The recording circuitry thereafter resumes recording upon being reconnected. If necessary, the patient 12 may choose to take a break and allow her skin to "breathe" between applications of the skin adhesion layer.

Throughout the monitoring period, the patient ideally makes regular entries in his diary 17, as described infra, which provides context that can help relate patient symptoms to the recorded ECG data, even where there are gaps in the monitoring due to replenishment of the skin adhesive layer or other factors. In a further embodiment, the monitor 15 includes an actimetry sensor, which measures gross motor activity undertaken by the patient, such as through walking, running, changing posture or sleep position, and other body motions, that can be temporally matched with diary entries during post-monitoring evaluation. Monitoring ends when the patient 12 removes the monitor 15 from his chest. Thereafter, the patient 12 sends the monitor 15 (or its ECG data recordings) to the referral center, along with his completed diary 17 (step E), as further described below with reference to FIG. 6. Upon receipt, a laboratory technician 23 or other personnel retrieves the recorded ECG data 25 and, if provided, the actimetry, from the monitor 15 (step F) for analysis, post-monitoring diagnosis, follow up, and referral, as further described below with reference to FIG. 7.

The tracking number 19 allows both the referral center and the patient 15 to follow the use of the monitor 15 from application through reading, diagnosis, and referral. In-clinic, the primary care physician 14 or his assistant use a computer, including a desktop, notebook, or tablet computer, or mobile computing device, such as a smart telephone, to access the RFID tags of the monitor 15 and envelope 18. The ability to ascertain the whereabouts and status of the monitor 15 and its recorded data at any point in the process is empowering. Thus, in response to an inquiry sent to the referral center by the patient 12 and keyed to the tracking number 19, the patient 12 can determine the status of ambulatory ECG monitoring, data retrieval, ECG data evaluation, any clinical findings, including findings of a cardiac rhythm abnormality, or a referral to an appropriate medical specialist. Primary care physicians can establish patient compliance. Cardiac specialists are able to reconstruct the steps leading up to a referral. The referral center maintains positive control. And patients are granted the ability to close the loop on their health care provisioning by knowing where they are in the diagnostic process, and, equally important, where they are headed in the process of their follow-up, subsequent care and therapy. In sum, patients are provided closure for their problem, which is increasingly infrequent in today's healthcare system.

Figure 2:
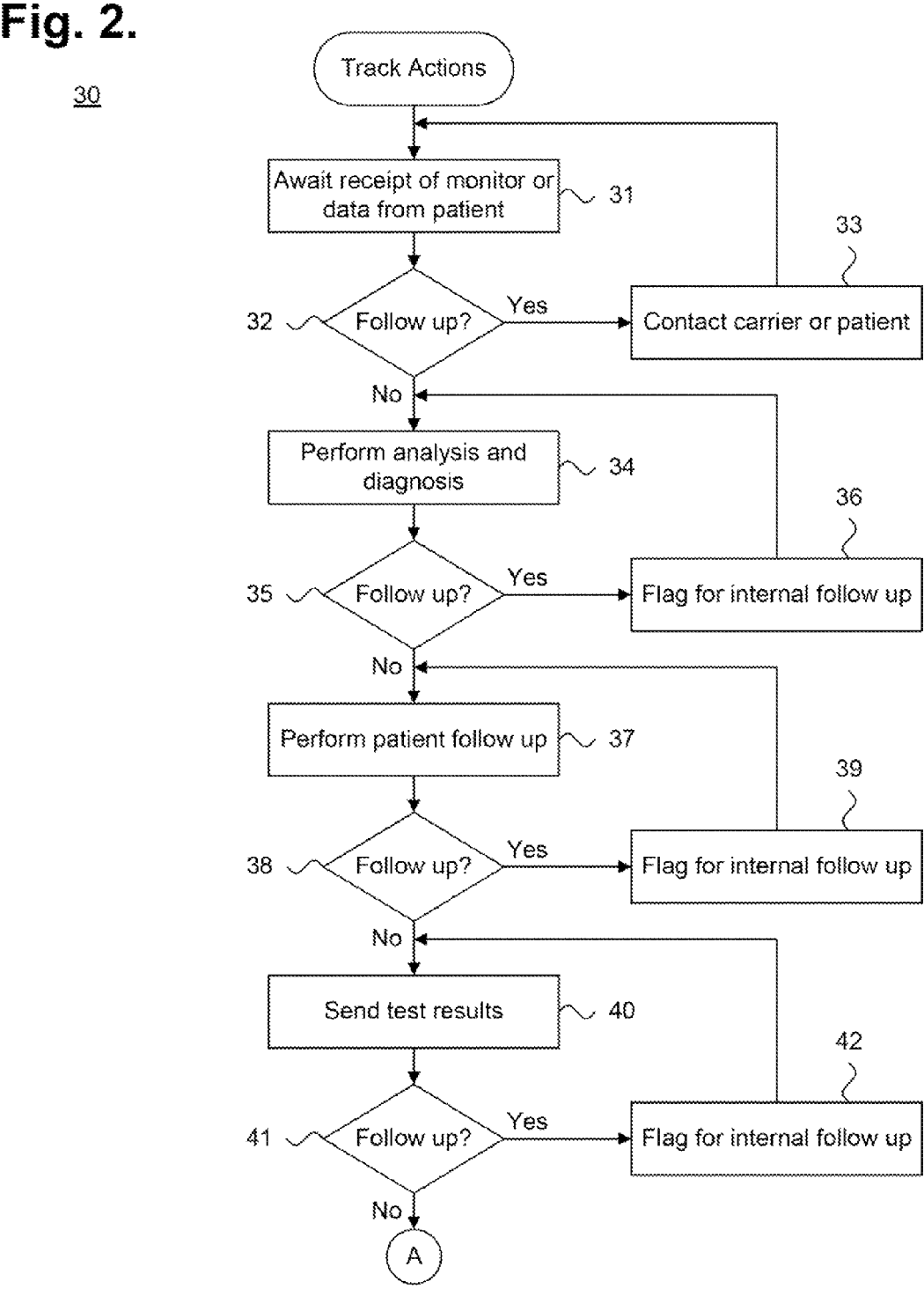
FIG. 2 is a flow diagram showing the tracking of actions by a referral center as used in conjunction with the method of FIG. 1.

Each monitor 15 and its recorded data are tracked using a combination of the tracking number 19 and a series of scheduled actions. The actions are tracked and coordinated by the referral center through an online database. FIG. 2 is a flow diagram showing the tracking of actions 30 by a referral center as used in conjunction with the method 10 of FIG. 1. The actions include:

(1) Each monitor 15 is expected to be sent off by the patient 12 and received at the referral center within a fixed amount of time following completion of monitoring (block 31). For instance, a period of 48 hours may be allotted for a patient 12 to provide the monitor 15 or its recorded data to the referral center, where the data is transmitted electronically in lieu of physically sending the monitor 15. Upon the expiry of 48 hours or other allotted time (block 32), the referral center will initiate follow up (block 33), which can include contacting the carrier, such as Federal Express, or the patient 12. Follow up may be electronic, for instance, by accessing an online package tracking database or sending text messages, or via phone or mail communication.

(2) Analysis and diagnosis is performed by the referral center within a fixed amount of time upon receipt of each monitor 15 or its recorded data (block 34). For instance, a period of 24 hours may be allotted for completing data analysis and diagnosis. Failure to complete analysis and diagnosis within the allotted time (block 35) is flagged for internal follow up by the referral center (block 36). A physician, either primary care or referred, or the patient 12 is permitted to inquire with the referral center into the nature of any delay.

(3) Follow up with the patient 12 is by the referral center is guaranteed within a fixed amount of time following completion of analysis and diagnosis (block 37). For instance, a period of 24 hours may be allotted for patient follow up, which can include contacting the patient 12 with status information, generating a referral to a cardiac specialist, and notifying the patient 12 of their cardiac specialist appointment. Failure to complete patient feedback within the allotted time (block 38) is flagged for internal follow up by the referral center (block 39). A physician, either primary care or specialist, or the patient 12 is permitted to inquire with the referral center into the nature of any delay.

(4) Where a referral to a cardiac specialist is generated, the test results and patient medical records must be sent to the referred physician within a fixed amount of time following patient follow up (block 40). For instance, a period of 24 hours may be allotted for forwarding the test results. The test results can be transmitted electronically to the referred physician. Patients 12 and authorized physicians can access the test results through a secure Web page. Failure to forward test results within the allotted time (block 41) is flagged for internal follow up by the referral center (block 42). A physician, either primary care or specialist, or the patient 12 is permitted to inquire with the referral center into the nature of any delay.

(5) The patient 12 is expected to confirm his appointment with the referred physician within a fixed amount of time following patient follow up (block 43). For instance, a period of 24 hours may be allotted for the patient 12 to confirm. The patient 12 can confirm electronically, for instance, by email or text message, or manually. Upon the expiry of 24 hours or other allotted time (block 44), the referral center will initiate follow up with the patient 12 (block 45). Follow up may similarly be electronic, voice or mail.

Figure 3:
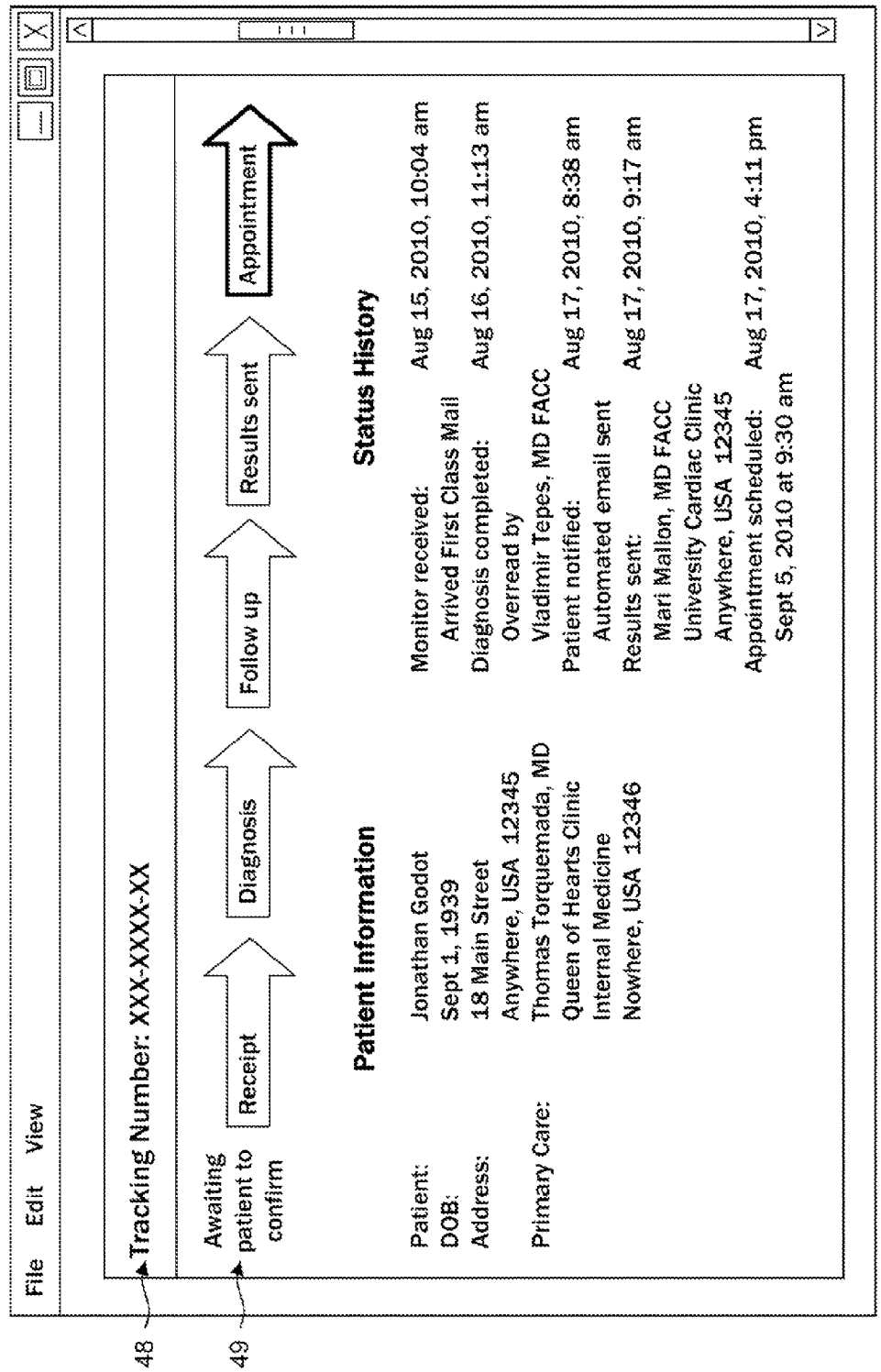
FIG. 3 is a screen shot showing, by way of example, a Web page for the tracking of actions by a referral center as used in conjunction with the method of FIG. 1.

In one embodiment, the referral center provides Web-based applications for physicians, their staff, and patients that enable them to access the database with proper authorizations and privacy protections, as further described below with reference to FIG. 3. Additionally, the referral center can send electronic status updates via email, text message, or automated telephone calls to the patients, as well as others, upon the completion of each of the foregoing actions, as well as other actions. In a further embodiment, the physicians, their staff, and the patients can also contact the referral center manually, such as via a toll free telephone number. For instance, a patient 12 may wish to speak to an on-call nurse at the referral center concerning the test results or their scheduled referral. Other ways to interface with the referral center are possible.

In one embodiment, status can be checked by accessing the referral center's Web site and entering the tracking number. FIG. 3 is a screen shot showing, by way of example, a Web page 47 for the tracking of actions 30 by a referral center as used in conjunction with the method 10 of FIG. 1. The Web page is viewable using a Web browser or similar application with online access as executed using a Web-capable device, including computer workstation, personal computer, personal digital assistant, programmable or "smart" mobile telephone, intelligent digital media player, mobile tablet computer, or other programmable stationary or portable electronic device.

The Web page 47 displays the status of the actions 30 undertaken following completion of ambulatory ECG monitoring. The patient 12 retrieves the Web page 47 by entering the tracking number 48 or other identifying information. The status of the testing 49 is then presented in a secure manner than ensures patient privacy, for instance, by using secure socket layer (SSL) communications security. The status information can include, for instance, a summary of the patient information on file and a history of the actions undertaken by the referral center. Other kinds of status information, forms of processing status inquiries, and of presenting status information are possible.

Figure 4:
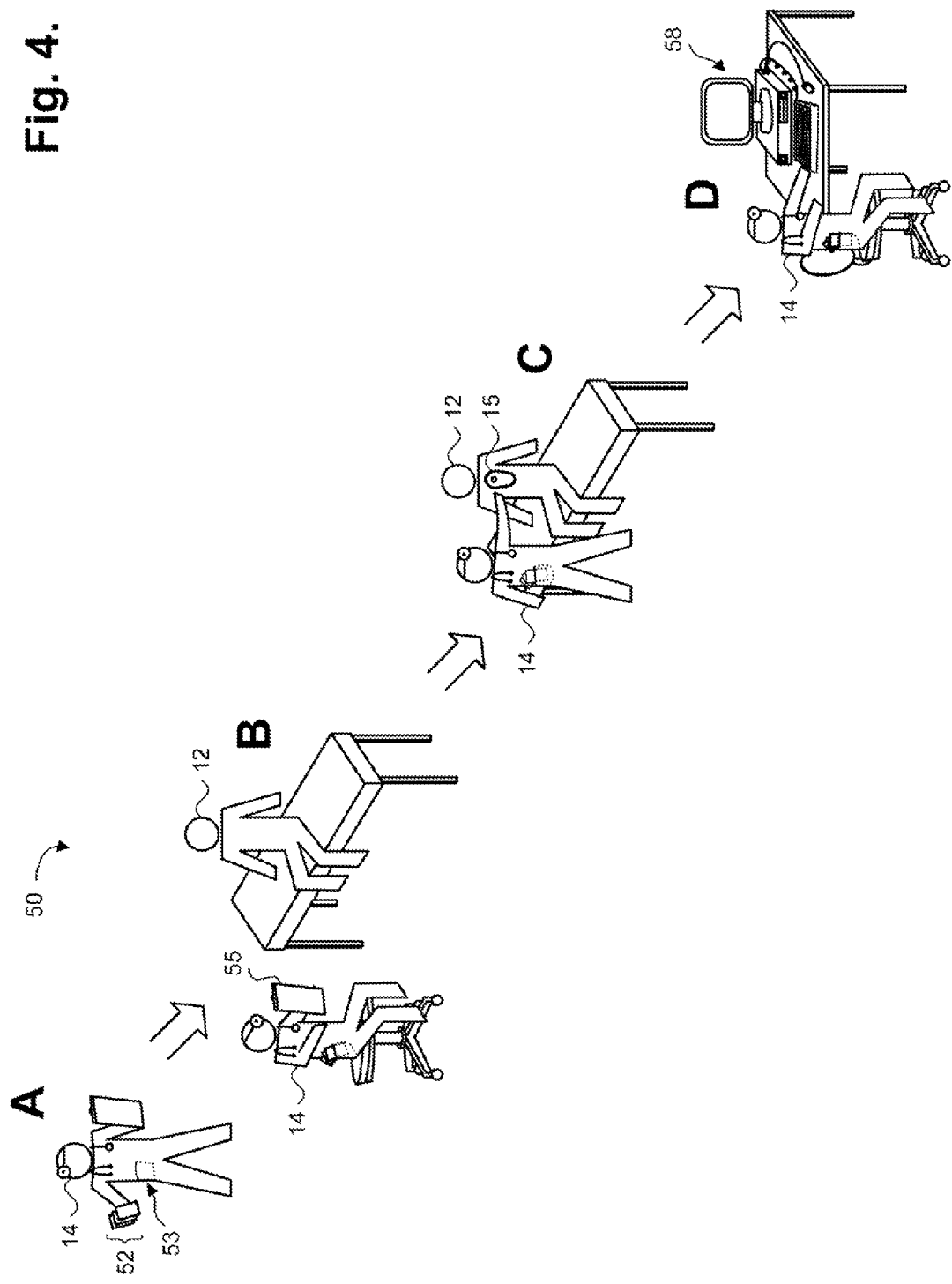
FIG. 4 is a diagram showing, by way of example, in-clinic application of the ambulatory ECG monitor of FIG. 1.

The monitor provides frontline primary care physicians with a simple and low-cost form of ambulatory ECG monitoring without the obstacles inherent in acquiring the device, the complexities and inefficiencies of calling and contacting referral offices, and the unacceptable costs in terms of time and repetitive travel that are attendant to conventional ambulatory ECG monitors. FIG. 4 is a diagram showing, by way of example, in-clinic application 50 of the ambulatory ECG monitor of FIG. 1. To encourage proactive diagnosis of arrhythmias or other conditions of medical concern, the ambulatory ECG monitors are provided as single use monitoring packages that are low cost and readily dispensable, such as described in commonly-assigned U.S. Patent application, entitled "Ambulatory Electrocardiographic Monitor and Method of Use," Ser. No. 12/901,444, filed Oct. 8, 2010, pending, and U.S. Patent application, entitled "Ambulatory Electrocardiographic Monitor for Providing Ease of Use in Women and Method of Use," Ser. No. 12/901,428, filed Oct. 8, 2010, pending, the disclosures of which are incorporated by reference. Other types of ambulatory ECG monitors could also be used.

The low cost and convenience of access of ambulatory ECG monitors encourages rapid patient diagnostic testing, which is currently underutilized in primary care medicine because of the inconvenience and difficulty generally encountered in accessing conventional ambulatory ECG monitors and the difficulty of diagnosis and receiving actionable information. Here, a primary care physician 14 can keep a set of the pre-packaged ambulatory ECG monitors 52 readily at-hand (step A), for instance, in his laboratory coat pocket 53 or on an examination room table. Ambulatory ECG monitoring can be undertaken in a wider range of circumstances than practicable with conventional forms of ambulatory monitoring, which entail significant care giver, patient, and financial burden. For instance, a primary care provider 14 can use the ambulatory ECG monitors 52 for evaluating the efficacy of new medications or other changes to patient care. Similarly, a series of ambulatory ECG monitors 52 can be used over the course of several months to establish a trending analysis for a patient 12 with particularly sporadic symptoms, such as episodic paroxysmal atrial fibrillation. The threshold of use is low enough and the back up reading support and expert referral, when necessary, are integral parts of the system. Thus, a primary care provider 14 can freely apply the ambulatory ECG monitors 52 without distraction from managed health care limits or concerns of being outside his range of expertise, both in the case of interpreting ambulatory ECG monitoring data and, importantly, in managing its results. In turn, the patient 12 receives in a timely manner the full spectrum of appropriate responses to his symptoms.

During examination, as appropriate, the primary care provider 14 takes a patient history 55 and performs a physical examination 39 (step B). A complete patient history 55 indicates how frequent the patients presumed arrhythmia arises, its duration, the severity of symptoms, heart rate, drug and dietary history, systematic illnesses, and family history of rhythm disturbances. The patient history 55 elicits major cardiovascular symptoms and how they may have varied over time. Classic cardiovascular symptoms can include chest discomfort, dyspnea, fatigue, edema, palpitations, syncope, coughing, hemoptysis, and cyanosis. The physical examination 39 includes findings from physical inspection, palpitation, percussion, and auscultation, which may help provide clues that link disparate aspects of the patient's presentation. Findings from the patient medical history 55 and physical examination 39 are used during subsequent online diagnosis by a server operated as part of the referral center, as further described below with reference to FIG. 7.

Figure 5:
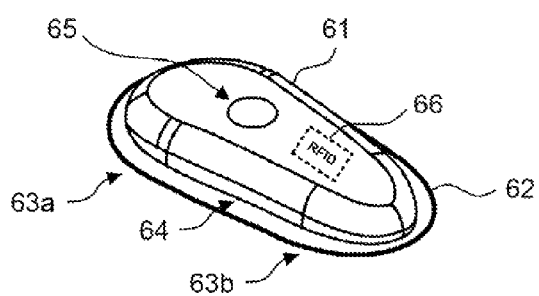
FIG. 5 is a diagram showing, by way of example, an ambulatory ECG monitor in accordance with one embodiment.

Through use of the monitor 15, both physicians and patients enjoy an ease-of-use not found with conventional ambulatory. ECG monitors. Ambulatory ECG monitoring can be initiated when indicated by patient condition or when otherwise considered appropriate by the physician 14. Referring briefly ahead to FIG. 5, each monitor includes a pair of leadless sensing electrodes 63a, 63b exposed on the underside of an adhesive layer 62 and connected to low cost ECG recording circuitry integrated in a compact single-use housing 61. Each monitor also includes an RFID tag 66 containing a unique identifier for the monitor that is either integrated with the ECG recording circuitry, or is embedded into the monitor's housing, such as within a foam-constructed cover. The RFID tag 66 is used during monitoring to associate a monitor 15 to a patient-specific tracking number 19 that can be used by the patient 12, referral center, and physician or staff to track the physical whereabouts of the monitor 15 and to determine the post-monitoring status of diagnosis and follow up care. The RFID tag 66 is accessed using standard RFID transmitter and receiver units.

Referring back to FIG. 4, the monitor 15 is placed on the patient's chest at midline, covering the center third of the sternum between the manubrium and the xiphoid process that is found at the inferior limit of the sternum (step C). The monitor 15 can be applied by the primary care physician 14, or an assistant, such as a nurse. This unique location for ECG monitor application and the monitor's small size allow for a uniformity of applicability by minimally trained physicians or even lay individuals. Application of the monitor 15 is no more difficult than applying a bandage over a wound. Monitor application takes a few seconds and is significantly more time and cost efficient than both making a cardiac specialist referral, which often requires writing letters and making telephone calls, or sending a patient to a hospital or major cardiology practice to access an ambulatory ECG monitor. Unlike application of the twelve leads used by standard Holter systems, non-expert individuals have the ability to successfully apply the monitor 15 without needing medical training or separate instruction. In addition, the midline sternum-centered location is ideal for demonstrating key ECG features of atrial activity, such as P-waves, as well as ventricular activity, such as R-waves.

In a further embodiment, ambulatory ECG monitoring can be initiated through self-care. Where available without a prescription, the patient 15 can simply obtain and apply an ambulatory ECG monitoring kit over-the-counter. Alternatively, the primary care provider 14 can call in a prescription to a pharmacy or other dispensary point-of-sale for the patient 12 to obtain a single use ambulatory ECG monitoring kit. The patient 12 may have already performed his own research as to his condition or spoken to a physician, nurse practitioner, or other health care professional about his perceived health concerns through telephonic "on-call" patient services. The patient 12 can request his primary care provider 14 to call in a prescription for an ambulatory ECG monitor. The patient thus avoids the need to see the primary care provider 14 in-person through an in-clinic appointment and can apply the monitor 15 himself.

Physical application of the monitor 15 is the only step required to initiate ambulatory ECG monitoring. Minimal to no primary care provider involvement need be undertaken prior to starting ambulatory ECG monitoring. Conventional follow up appointments with an ECG monitoring laboratory and a primary care physician-referred cardiac specialist are unnecessary, at least at this point. Instead, the patient 12 takes care of returning the monitor 15, or, in a further embodiment, just the ECG data recorded by the monitor 15, for reading and follow up by the referral center, along with the diary 17 as maintained by the patient 12 throughout monitoring.

Finally, contemporaneous to application of the monitor 15, the primary care provider 14, or an assistant, electronically matches the monitor 15 to the patient 12 using the monitor's unique identifier that is stored in the RFID tag 66 (step D). Each monitor 15 is registered for use by the patient and is generally for one-time use. An RFID transceiver-equipped computer 58, including a desktop, notebook, or tablet computer, or mobile computing device, such as a smart telephone, scans the RFID tag 66 and records the monitor's unique identifier into a database centrally maintained by the referral center online.

A small, anatomically adaptive, and single-use ambulatory ECG monitor is applied in-clinic by a primary care provider 14, at home by the patient 12, or by other healthcare or lay individuals to record ECG data over an extended time period, while the patient 12 engages in activities of daily living. FIG. 5 is a diagram showing, by way of example, an ambulatory ECG monitor 60 in accordance with one embodiment. The monitor 60 is placed on the midline of the patient's chest and centered over the sternum. Conforming fit and secure adhesion to the inherently uneven surface of a midline sternum-centered location are provided through two interconnected structures: a flexible housing for the electronic circuitry and standoff-separated skin adhesion assembly specifically designed to adapt to a variable contour sternal surface. A waterproof housing 61 encloses ECG recording circuitry. The housing 61 is independently suspended through a set of standoffs that forms a gap 64 of about 2.5 mm (0.1 in) between an adhesive layer 62 that conformably adheres to the patient's skin and the housing 61. A set of at least two electrodes 63a, 63b are received in holes or "gel wells" formed through the standoffs and are exposed at the bottom surface of the adhesive layer 62.

Physically, when viewed from above, the monitor 60 has an elongated triangular shape with rounded vertices with dimensions of approximately 3.8 cm (1.5 in) wide and 7.6 cm (3.0 in) long. The monitor 60 weighs about 14.2 g (0.5 oz) when assembled with electrodes and a waterproof housing for the ECG recording circuitry, although a weight of up to 28 g (1.0 oz) would be acceptable. The electrodes 63a, 63b are spaced less than 6 cm apart, and, when adhered to the patient, are aligned and placed midline sternum-centered. In one embodiment, two electrodes are used, although three or more electrodes could also be used. When adhered onto a patient's sternum, the narrowest part of the monitor 41 faces downwards towards the patient's feet. On a female patient, the narrow part of the monitor 60 fits partway into the upper intermammary cleft. In a further embodiment, the monitor 60 includes a patient-operable button 65 that allows the patient 12 to set an electronic marker in the recorded ECG, such as when she feels the onset of a symptom or episode. During post-monitoring evaluation, each electronic marker is matched to the ECG and diary entries.

Figure 6:
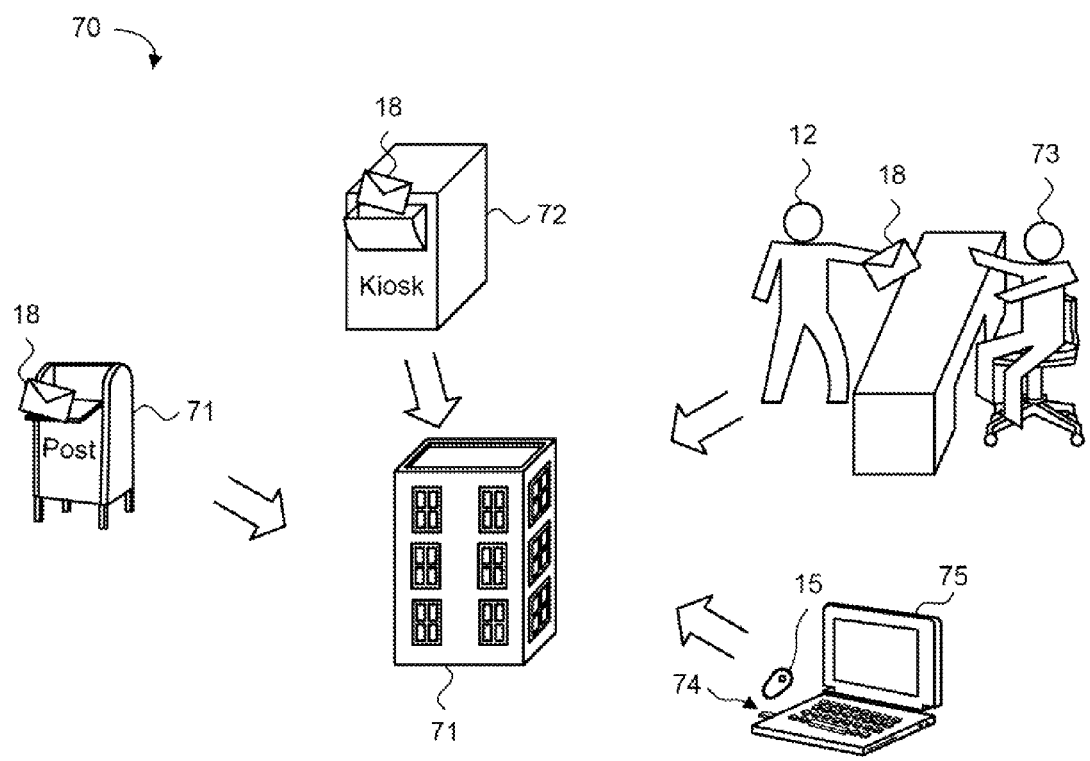
FIG. 6 is a diagram showing, by way of example, delivery of the ambulatory ECG monitor of FIG. 1.

Ambulatory ECG monitoring begins with clinic application of a monitor and ends upon removal of the monitor by the patient, who must then provide the recorded ECG data to the referral center. FIG. 6 is a diagram showing, by way of example, delivery 70 of the ambulatory ECG monitor 15 of FIG. 1. The referral center 71 is an organizational entity typically independent from the primary care provider's clinic. The referral center 71 provides ambulatory ECG data reading, analysis, diagnosis, and patient referral and follow up, such as described in commonly-assigned U.S. Patent application, entitled "Computer-Implemented System and Method for Facilitating Patient Advocacy through Online Healthcare Provisioning," Ser. No. 12/901,433, filed Oct. 8, 2010, pending, the disclosure of which is incorporated by reference.

To encourage appropriate use by primary care physicians and patients alike, the referral center 71 offers several channels for receiving used monitors 15. First, the monitor 15 can be physically sent to the referral center 71 via a package carrier, delivery service, or postal service. Delivery can be as simple as placing the monitor 15 into a pre-addressed sealable envelope 18 received from the primary care physician's office and dropping the envelope 18 into delivery box 71, post office, shipping center, and the like. Second, the sealable envelope 18 could be sent using a courier or delivery service that is contracted to specifically deliver used monitors 15 to the referral center 71. The patient 12 places the monitor 15 into the sealable envelope 18, which is then dropped into a kiosk 72 or other pickup location designated by the courier or package delivery service. Finally, the patient 12 could just return the monitor 15 in the sealable envelope 18 to administrative personnel 73 at the clinic, a "help" desk at a hospital, or other locations manned by health care staff.

In a further embodiment, instead of physically returning the used monitor 15 to the referral center 71, the recorded ECG data can be delivered electronically. For example, the monitor 15 can include a USB or similar standardized data exchange interface 74 for plugging into a computer 75, including a desktop, notebook, or tablet computer, or mobile computing device, such as a smart telephone. Alternatively, the monitor 15 could include a removable standardized memory module, such as a Secure Data memory card. The personal computer reads the recorded ECG data and patient information and electronically transmits the data read to the referral center, either by dedicated private communications circuit or publicly-available data communications network, such as the Internet. As well, the monitor 15 could incorporate a wired data connection, such as an IEEE 802.3 Ethernet interface, or a wireless transmitter using, for instance, Bluetooth or Wireless Fidelity ("WiFi") technology to wirelessly relay the recorded ECG data to the referral center 71. Other forms of physical or electronic delivery of recorded ECG data are possible.

Figure 7:
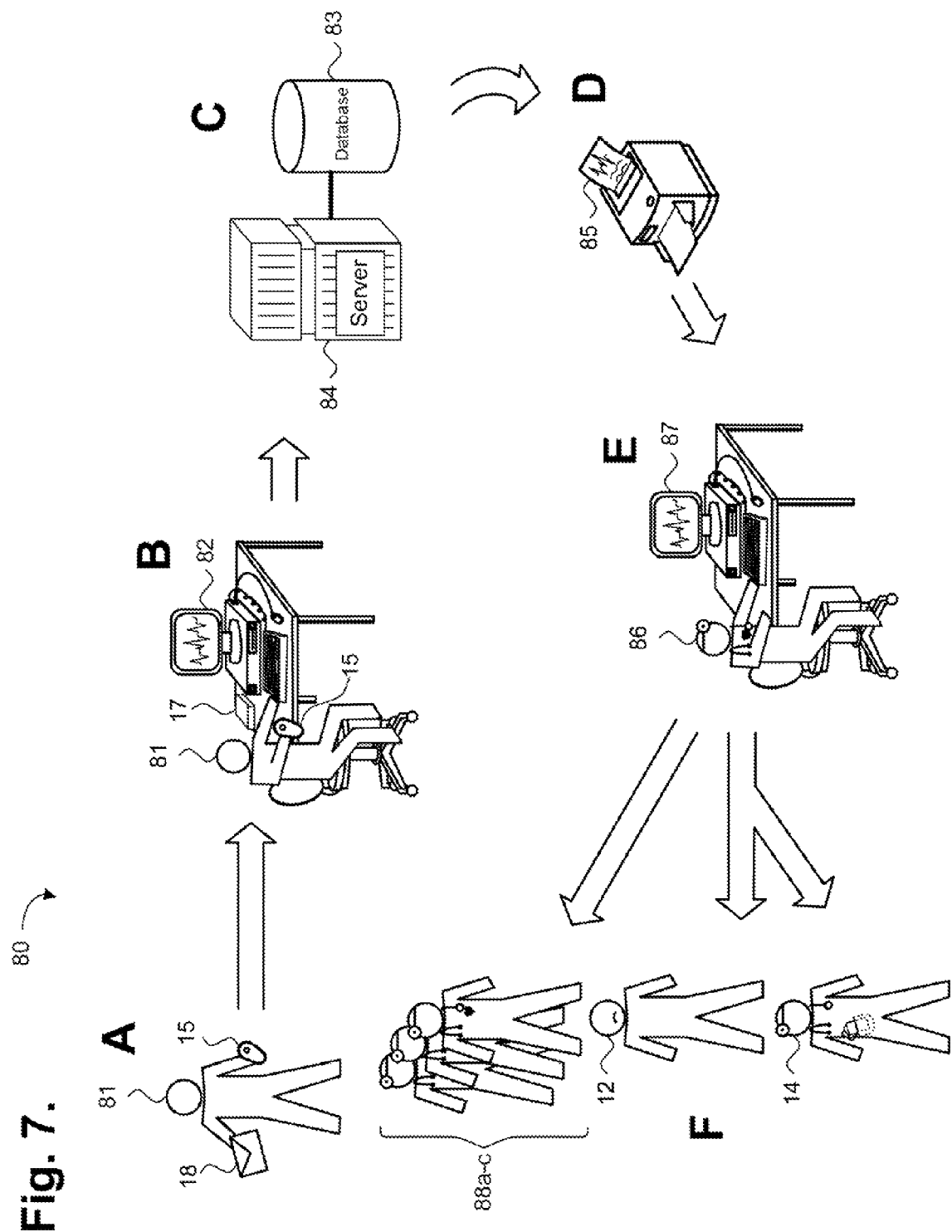
FIG. 7 is a diagram showing, by way of example, evaluation of patient ECG data retrieved following the ambulatory monitoring of FIG. 1.

The low cost ambulatory ECG monitor facilitates flexible implementation with consistent and clinically-sound medical follow up that ensures resolution of the patient's arrhythmic heart disorder concerns, in other words, a closed loop system from the patient's perspective. FIG. 7 is a diagram showing, by way of example, evaluation 80 of patient ECG data retrieved following the ambulatory monitoring of FIG. 1. The referral center performs data interpretation and follow up with the patient directly.

The referral center first processes receipt of the monitor 15. If the monitor 15 is physically sent in a sealable envelope 18, a laboratory specialist 81 first ensures that the tracking number or other confirmatory information assigned to the monitor 15 correctly matches the sealable envelope 18 (step A). If mismatched, the laboratory specialist 81 notifies the primary care provider 14 that a problem exists with either the wrong sealable envelope having been provided to the patient 12, or incorrect encoding of the monitor 15. If the monitor 15 and sealable envelope 18 pairing is confirmed, the laboratory specialist 81 electronically retrieves the recorded ECG data 82 from the monitor 15 into a computer workstation or other intermediate electronic data repository (step B). The laboratory specialist 81 also processes any further patient medical information provided with the sealable envelope 18, such as the patient's diary 17. The first two steps are skipped if the recorded ECG data is electronically sent directly to the referral center 71.

The referral center 71 maintains a database 83 within which recorded ECG data 82, medical records and other quantitative information, and diary entries and other qualitative information are stored for each patient 12, as identified using the tracking number 19. A server 84, or similar centralized computational device, evaluates the recorded ECG data 82 to identify cardiac rhythm abnormalities. The server includes those components conventionally found in general purpose programmable devices, such as a central processing unit, volatile memory, input and output ports, user display, keyboard or other input device, network interface, and non-volatile mass storage. Other components are possible.

The electrocardiogram recorded by the monitor 15, like all electrocardiograms, is amplified, filtered, and digitized over the range of 0.05 Hertz (Hz) to 150 Hz bandwidth for adults, and up to a 250 Hz bandwidth for children with a sampling rate of between one Kilohertz (KHz) and two KHz. ECG tracings are compared by the server 84 to medical diagnostic criteria to identify specific cardiac abnormalities. The criteria may be the sole basis for initial diagnosis. However, the initial diagnosis may also be correlated against any clinical, physiological, or pharmacological findings available in the patient's electronic medical records. The most common diagnostic criteria are based on statistical correlations between well known cardiac and other potential disease states with particular cardiac rhythm patterns appearing in ECGs and are well represented in many textbooks of cardiology, such as P. Libby et al., "Braunwald's Heart Disease—A Textbook of Cardiovascular Medicine," Chs. 11 and 12 ($8^{th}$ ed. 2008), the disclosure of which is incorporated by reference. Innumerable diagnostic algorithms have been devised to identify various disease states for these disorders. Consequently, for purposes of both clarity and brevity, the discussion herein focuses on the sequence of events that unfold should a particular rhythm disorder become manifest on an ECG.

In diagnosing cardiac arrhythmia, some arrhythmias are highly symptomatic, yet are not associated with any adverse outcomes, such as premature ventricular complexes. Other arrhythmias may present with no symptoms, yet may still present a significant risk of stroke, such as atrial fibrillation. Accordingly, in addition to the diagnostic criteria of the purely ECG-based data, the patient's medical history and the daily entries in the patient's diary 17 can be persuasive in reaching a diagnosis, or guiding further diagnostic testing or physician referral. Inquiry into the patient's medical history examines:

mode of onset of arrhythmic episodes: For example, palpitations that occur while exercising, or when frightened or angry, signify different cardiac proclivities than palpitations that occur at rest or which awaken the patient from sleep. Similarly, lightheadedness or syncope when frightened or having blood drawn is significantly different than syncope without warning, with the latter carrying a more serious implication and is more often associated with serious rhythm abnormalities.

mode of termination of ectopic episodes: Palpitations reliably terminated by breath holding or the performance of the Valsalva or other vagal maneuvers can be a reliable indicator of a congenital rhythm abnormality, like atrio-ventricular nodal re-entry.

Other inquiries are possible, such as those regarding cardiac or lung disease status, or overall health. The diary entries can be temporally matched to cardiac rhythm patterns in the recorded electrocardiogram, which can assist with pairing physiological symptoms identified in the ambulatory ECG data to the patient's activities of daily living and contemporaneous symptomatic complaints. Other uses of the diary entries and patient medical history are possible.

Based on established diagnostic criteria, a set of diagnostic findings 85 is generated by the server 84 (step D). The findings 85, along with the patient's diary entries, can then be provided to a clinical specialist 86 (step E), such as a cardiologist, who has pre-contracted with or been retained by the referral center 71 to interpret diagnostic findings 85 and to make a formal medical diagnosis 87. The diary entries help temporally link objective symptomatic data recorded by the monitor to subjective observations made by the patient concerning his activities and physical complaints during the monitoring period. Diary entries are particularly helpful in placing patient symptomatic complaints in context. Unfortunately, a common outcome in modern managed care medical practices, where patients rarely see the same physician, key circumstances attendant to a complaint may be overlooked or forgotten by the original attending physician who ordered the ambulatory ECG recording in the first place. By storing the patient's medical history, electronic medical records, ambulatory ECG recording, and diary entries in one centralized database 83 maintained by the referral center 71 and by pre-contracting with expert assistance in the geographic area in which the patient lives, a patient can be given immediate and, importantly, pertinent referrals and thereby pertinent medical care.

Based on the diagnosis 87, the referral center 71, and not the initial source of ECG monitor application, that is, the primary care physician 14, performs medical follow up directly with the patient 12, which can include sending the diagnosis 87 to one or more clinical specialists 88a-c (step F), such as cardiologists or cardiac electrophysiologists when the findings indicate a cardiac rhythm disorder, and notifying the patient 12 of the follow up referrals that were arranged. This step not only jump starts the patient management process in the event of a serious diagnosis, but also ensures that patients receive appropriate care and are not lost in the confusing shuffle of modern medicine. The patient 12 remains an active part of the care provisioning and can inquire at any stage as to the whereabouts and status of his test results and follow up and the health care loop is thereby closed, without the patient being left in the open, that is, as a passive actor awaiting notification that may, or may not, happen. The primary care provider 14 is also notified of the type of follow up taken, but is not a part of the continuing health care provisioning process: Other forms of patient follow up are possible.

Figure 8:
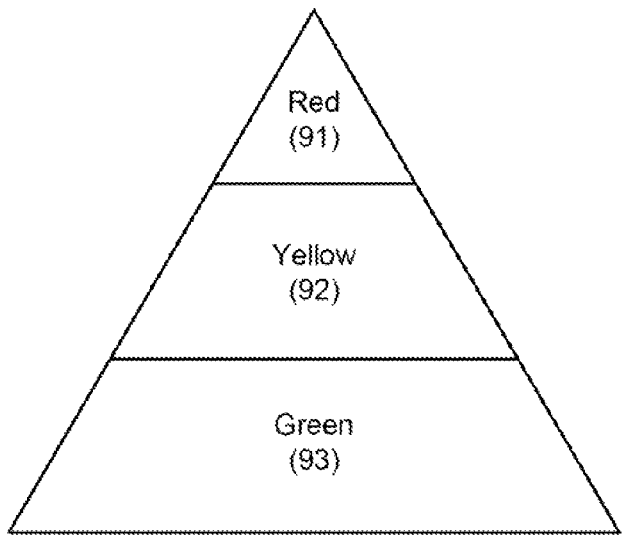
FIG. 8 is a block diagram showing, by way of example, levels of triage use by the referral center of FIG. 6.

The referral center 71 triages medical follow up using, for instance, a three-tiered referral scheme. FIG. 8 is a block diagram showing, by way of example, levels of triage 90 use by the referral center 71 of FIG. 6. At the highest level "red" 91, a potentially life-threatening cardiac rhythm disorder is diagnosed, such as ventricular tachycardia, asystole or heart block. An appointment is automatically booked with a clinical specialist 88a-c, and the patient 12 is notified of the appointment immediately. His primary care provider 14 is also provided the diagnosis 87 and notice of the patient's cardiac specialist appointment and the urgency behind the referral. In a further embodiment, several clinical specialists 88a-c can receive the diagnosis 87 and the clinical specialist 88a-c that is ultimately assigned the referral is selected based on a selection criteria, such as first-to-respond or round-robin. Other selection criteria are possible, for instance, closest geographic location, earliest appointment opening, field of interest or expertise, such as a cardiac electrophysiologist specializing in heart rhythm disorders, and the like.

At the second level "yellow" 92, a non-cardiac rhythm diagnosis 87 is made and the patient 12 is referred to a non-cardiac rhythm specialist (not shown). For example, an ST segment depression warrants referral to a cardiologist specializing in coronary disease management, and not to a cardiac electrophysiologist. As well, widening of the QRS complex may best indicate the need for a referral to a heart failure expert, while QT interval variation indicates appropriate follow up with an internal medicine physician to consider, for instance, drug-induced QT prolongation and the need for alternative drug therapy, for example, a different antibiotic. A loss of consciousness, despite normal laboratory ECG findings, implies non-heart rhythm problems and may indicate a need for referral to a neurologist or vascular surgeon. Other types of healthcare disorders can be diagnosed and referred to the appropriate physician in a timely and efficient manner without wasting time for either the patient or the primary care provider.

At the lowest level "green" 93, the patient 12 is considered normal or healthy, or at least with no discernible illness. No referral need be made and the patient 12 can be reassured, such as through a message from the referral center 71, that their heart rhythm is normal or that the symptoms may arise from a non-rhythm problem. Other levels of referrals and triage are possible.

Figure 9:
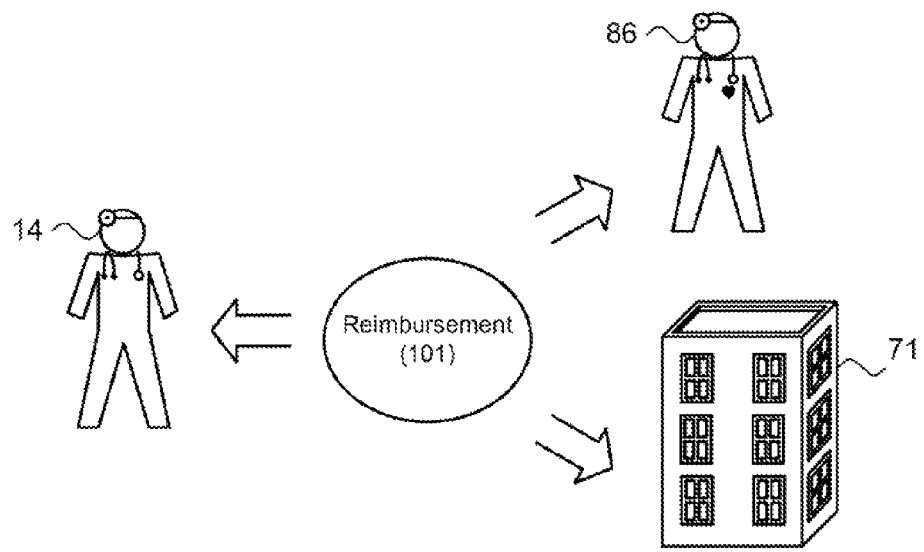
FIG. 9 is a diagram showing a reimbursement scheme for health care provisioning participants in accordance with one embodiment.

Reimbursement for medical services provided is a reality of managed care. The ambulatory ECG monitor 15 can be used within a medical insurance reimbursement structure that compensates the major service providers commensurate with the work performed. FIG. 9 is a diagram showing a reimbursement scheme 100 for health care provisioning participants 14, 71, 86 in accordance with one embodiment. Each of the primary care provider 14, the referral center 71, and the retained clinical specialist 86 provide services respectively in the initiation of ambulatory ECG monitoring, data collection and initial analysis, and interpretative over read of a patient's ambulatory ECG data 82, activities that can entitle each party to some form of compensable reimbursement. For instance, the primary care provider 14 can receive reimbursement comparable to in-clinic laboratory testing for application of a monitor 15 to the patient 12. The referral center 71 bears the onus of the costs for consumable goods, infrastructure, and liaison between the patient 12, the primary care provider 14, and, when appropriate, cardiac specialists 97a-c. Thus, the referral center 71 can receive reimbursement for providing the consumable goods, that is, the monitors 15, sealable envelopes 18, and diaries 17 to the primary care providers 14, or through over-the-counter or pharmaceutical channels, as appropriate. The referral center 71 also can receive reimbursement for consolidating patient medical histories and electronic medical records and for the reading, processing, and storage of recorded ECG data 82. Finally, the retained clinical specialist 86 can receive reimbursement comparable to a professional reading of medical findings. Other reimbursement schemes and tiers are possible.

While the invention has been particularly shown and described as referenced to the embodiments thereof, those skilled in the art will understand that the foregoing and other changes in form and detail may be made therein without departing from the spirit and scope.

What is claimed is:

1. A computer-implemented method for evaluating ambulatory electrocardiographic (ECG) monitoring of cardiac rhythm disorders, comprising the steps of:
   registering a patient online and assembling medical records for the patient;
   registering an ambulatory ECG monitor, including a monitor RFID tag, that comprises leadless integrated sensing electrodes independently suspended from a flexible housing that encloses an ECG recording circuitry connected to the electrodes, to the patient;
   assigning a tracking number to the monitor in relation to an ambulatory ECG monitoring and matching the tracking number to the patient;
   associating the tracking number with an envelope RFID tag accompanying an envelope in which to send the monitor for an evaluation upon a completion of the ambulatory ECG monitoring;
   tracking the physical whereabouts of the monitor through the tracking number of the monitor RFID tag and the envelope RFID tag prior to receipt of the monitor for the evaluation;
   retrieving an electrocardiogram from the recording circuitry;
   evaluating the electrocardiogram and the medical records for the patient against diagnostic criteria comprising statistical correlations of cardiac disease states and cardiac rhythm patterns using a processor;
   following up with the patient within a fixed, predetermined amount of time after evaluating the electrocardiogram and medical records; and
   upon making a finding of a cardiac rhythm abnormality when the diagnostic criteria is met, automatically referring the patient to a cardiac rhythm specialist online, including sending the cardiac rhythm abnormality finding and automatically scheduling an appointment for the patient with the cardiac rhythm specialist,
   wherein the steps are performed by a suitably programmed computer.

2. A method according to claim 1, further comprising:
   providing the tracking number to the patient; and
   in response to an online inquiry by the patient, determining a status of the evaluation and referral keyed to the tracking number.

3. A method according to claim 2, wherein the status concerns one or more of the ambulatory ECG monitoring, the retrieval of the electrocardiogram, the evaluation of the electrocardiogram, the finding of a cardiac rhythm abnormality, and the referral to a cardiac rhythm specialist.

4. A method according to claim 3, further comprising:
   setting a time period for one or more of the completion of the ambulatory ECG monitoring, the retrieval of the electrocardiogram, the evaluation of the electrocardiogram, the finding of a cardiac rhythm abnormality, and the referral to a cardiac rhythm specialist; and
   undertaking a follow up upon expiry of one or more of the time periods.

5. A method according to claim 1, further comprising:
   electronically sending the electrocardiogram for the evaluation from the recording circuitry directly upon the completion of the ambulatory ECG monitoring.

6. A method according to claim 1, wherein the monitor is placed on the patient's chest at midline, covering the center third of the sternum and centered between the manubrium and the xiphoid process on the inferior border of the sternum.

7. A computer-implemented method for diagnosing cardiac rhythm disorders through recorded ambulatory electrocardiograms, comprising the steps of:
registering a patient online with a referral center and assembling medical records for the patient in a centralized database maintained by the referral center;
registering an ambulatory electrocardiographic (ECG) monitor, including a monitor RFID tag, that comprises leadless integrated sensing electrodes independently suspended from a flexible housing that encloses an ECG recording circuitry connected to the electrodes, to the patient;
assigning a tracking number to the monitor in relation to an ambulatory ECG monitoring and matching the tracking number to the patient in the database;
associating the tracking number with an envelope RFID tag accompanying an envelope in which to send the monitor for an evaluation upon a completion of the ambulatory ECG monitoring;
tracking the physical whereabouts of the monitor through the tracking number of the monitor RFID tag and the envelope RFID tag prior to receipt of the monitor for the evaluation;
following the completion of the ambulatory ECG monitoring by the patient, performing analysis and referral through the referral center, comprising:
providing a status upon demand regarding the analysis and referral to the patient keyed to the tracking number;
retrieving an electrocardiogram from the recording circuitry; and
evaluating the electrocardiogram and the medical records for the patient against diagnostic criteria comprising statistical correlations of cardiac disease states and cardiac rhythm patterns using a processor;
following up with the patient within a fixed, predetermined amount of time after evaluating the electrocardiogram and medical records; and
upon making a finding of a cardiac rhythm abnormality when the diagnostic criteria is met, automatically undertaking a direct referral, comprising:
setting an appointment for the patient with a cardiac rhythm specialist online, including sending the electrocardiogram, medical records, and cardiac rhythm abnormality finding; and
notifying the patient of the appointment with confirmation,
wherein the steps are performed by a suitably programmed computer.

8. A method according to claim 7, the diagnostic criteria further comprising at least one of: identifying physiological symptoms comprising one or more of arrhythmic episodes and ectopic episodes, as recorded during the monitoring period; determining a mode of onset of each arrhythmic episode; determining a mode of termination of each ectopic episode; and comparing the physiological symptoms, the mode of onset of each arrhythmic episode, and the mode of termination of each ectopic episode to statistical correlations of cardiac rhythm patterns indicating possible cardiac disease states.

9. A method according to claim 7, further comprising one or more of: timing receipt of the monitor from the patient following the completion of the ambulatory ECG monitoring; timing performance of the analysis and referral of the patient; timing notifying the patient; timing sending of the sending the electrocardiogram, medical records, and cardiac rhythm abnormality finding; and timing confirmation of the patient's appointment, wherein a time period for follow up is triggered if any one of the timings exceed a set time period.

10. A method according to claim 9, wherein the follow up is undertaken by the referral center.

11. A method according to claim 7, further comprising:
registering an electronically-stored diary to the patient with the referral center under the tracking number;
recording entries into the diary as provided by the patient contemporaneous to the ambulatory ECG monitoring;
temporally matching the diary entries to cardiac rhythm patterns found in the electrocardiogram; and
pairing the physiological symptoms with the diary entries.

12. A method according to claim 11, further comprising one or more of:
directly recording the diary entries into the diary in electronic form;
electronically transcribing the diary entries from dictated verbal form; and
electronically transcribing the diary entries from written form.

13. A method according to claim 7, further comprising:
sensing disconnection of the recording circuitry from the electrodes during the monitoring; and
sending reconnection of the recording circuitry to electrodes and resuming the monitoring.

14. A method according to claim 7, wherein the medical records for the patient comprise one or more of monitored patient identification data, prior electrocardiograms, laboratory results, physical examination results, exercise testing results, and medical history.

15. A method according to claim 7, wherein the monitor is placed on the patient's chest at midline, covering the center third of the sternum and centered between the manubrium and the xiphoid process on the inferior border of the sternum.

16. A computer-implemented method for automated diagnosis and follow up ambulatory electrocardiographic monitoring, comprising the steps of:
enrolling a patient in a referral center;
registering an ambulatory electrocardiographic (ECG) monitor, including a monitor RFID tag, to the patient;
assigning a tracking number to the monitor in relation to an ambulatory ECG monitoring and matching the tracking number to the patient;
associating the tracking number with an envelope RFID tag accompanying an envelope in which to send the monitor for an evaluation upon a completion of the ambulatory ECG monitoring;
tracking the physical whereabouts of the monitor through the tracking number of the monitor RFID tag and the envelope RFID tag prior to receipt of the monitor for the evaluation;
retrieving an electrocardiogram from a recording circuitry of the ambulatory electrocardiographic monitor following the ambulatory ECG monitoring;
evaluating the electrocardiogram against diagnostic criteria comprising statistical correlations of cardiac disease states and cardiac rhythm patterns appearing in the electrocardiogram during the ambulatory monitoring using a processor; and
automatically performing follow up care of the patient through the referral center based on outcomes from the evaluation of the electrocardiogram within a fixed, predetermined amount of time after evaluating the electrocardiogram,
wherein the steps are performed by a suitably programmed computer.

17. A method according to claim 16, further comprising:
upon making a finding of a cardiac rhythm abnormality when the diagnostic criteria is met, directly referring the monitored patient and providing the finding and electrocardiogram to a cardiac rhythm specialist online.

18. A method according to claim 16, further comprising:
upon making a finding of a non-cardiac rhythm abnormality, directly referring the monitored patient and providing the finding and electrocardiogram to a non-cardiac rhythm specialist online.

19. A method according to claim 16, further comprising:
upon making a finding of no apparent health abnormalities based on the electrocardiogram, notifying the monitored patient.

20. A method according to claim 16, wherein the monitor is placed on the patient's chest at midline, covering the center third of the sternum and centered between the manubrium and the xiphoid process on the inferior border of the sternum.

\* \* \* \* \*